(12) United States Patent
Kameshima et al.

(10) Patent No.: US 7,227,926 B2
(45) Date of Patent: Jun. 5, 2007

(54) IMAGING APPARATUS AND IMAGING SYSTEM

(75) Inventors: Toshio Kameshima, Kumagaya (JP); Tadao Endo, Honjo (JP); Tomoyuki Yagi, Chofu (JP); Katsuro Takenaka, Kodama-gun (JP)

(73) Assignee: Canon Kabushiki Kaisha, Tokyo (JP)

( * ) Notice: Subject to any disclaimer, the term of this patent is extended or adjusted under 35 U.S.C. 154(b) by 116 days.

(21) Appl. No.: 11/088,775

(22) Filed: Mar. 25, 2005

(65) Prior Publication Data

US 2005/0220270 A1  Oct. 6, 2005

(30) Foreign Application Priority Data

Mar. 31, 2004  (JP)  ............................. 2004-107201

(51) Int. Cl.
*H05G 1/64* (2006.01)
(52) U.S. Cl. ..................................... 378/98.9; 378/98.8
(58) Field of Classification Search ................ 378/62, 378/64, 91, 98, 98.7, 98.8, 98.9, 98.11, 116
See application file for complete search history.

(56) References Cited

U.S. PATENT DOCUMENTS

| | | | | |
|---|---|---|---|---|
| 6,333,963 B1 * | 12/2001 | Kaifu et al. | ................ | 378/98.2 |
| 6,952,015 B2 | 10/2005 | Kameshima | ............ | 250/370.11 |
| 6,952,464 B2 | 10/2005 | Endo | ........................ | 378/98.11 |
| 6,985,555 B2 | 1/2006 | Endo | ........................ | 378/98.11 |
| 7,002,157 B2 | 2/2006 | Kameshima | ............ | 250/370.11 |
| 7,042,979 B2 * | 5/2006 | Ikeda | ......................... | 378/98.8 |
| 2003/0223539 A1 * | 12/2003 | Granfors et al. | ............ | 378/98.8 |
| 2005/0109927 A1 | 5/2005 | Takenaka et al. | ......... | 250/252.1 |
| 2005/0173645 A1 | 8/2005 | Endo | ...................... | 250/370.11 |
| 2005/0199834 A1 | 9/2005 | Takenaka et al. | ............ | 250/580 |
| 2005/0200720 A1 | 9/2005 | Kameshima et al. | ...... | 348/220.1 |
| 2005/0220269 A1 | 10/2005 | Endo et al. | .................. | 378/114 |
| 2005/0264665 A1 | 12/2005 | Endo | .......................... | 348/294 |
| 2006/0043261 A1 | 3/2006 | Matsuda et al. | .......... | 250/208.1 |
| 2006/0054834 A1 | 3/2006 | Kameshima | ........... | 250/370.11 |

FOREIGN PATENT DOCUMENTS

| | | | |
|---|---|---|---|
| JP | 2003-244557 | | 8/2003 |
| WO | WO 03/057039 | * | 7/2003 |

\* cited by examiner

*Primary Examiner*—Edward J. Glick
*Assistant Examiner*—Jurie Yun
(74) *Attorney, Agent, or Firm*—Fitzpatrick, Cella, Harper & Scinto

(57) ABSTRACT

An X-ray image radiographing system comprises an X-ray generator, a detection unit, a correction unit for performing a correction processing for the data outputted from the detection unit, and an output unit for outputting data processed by the correction unit. Moreover, it comprises a control unit for controlling the detection unit, the X-ray generator and the correction unit, a radiographing condition memory accessible by the control unit, a radiographing button for making a radiographing request to the control unit, a radiographing mode setting unit 106 for setting a radiographing mode in the control unit, and a photo timer having an AE function. The radiographing mode setting unit may be constituted of a workstation. Thereby, it is possible to provide an image radiographing apparatus and system capable of easily coping with a plurality of radiographing modes.

18 Claims, 15 Drawing Sheets

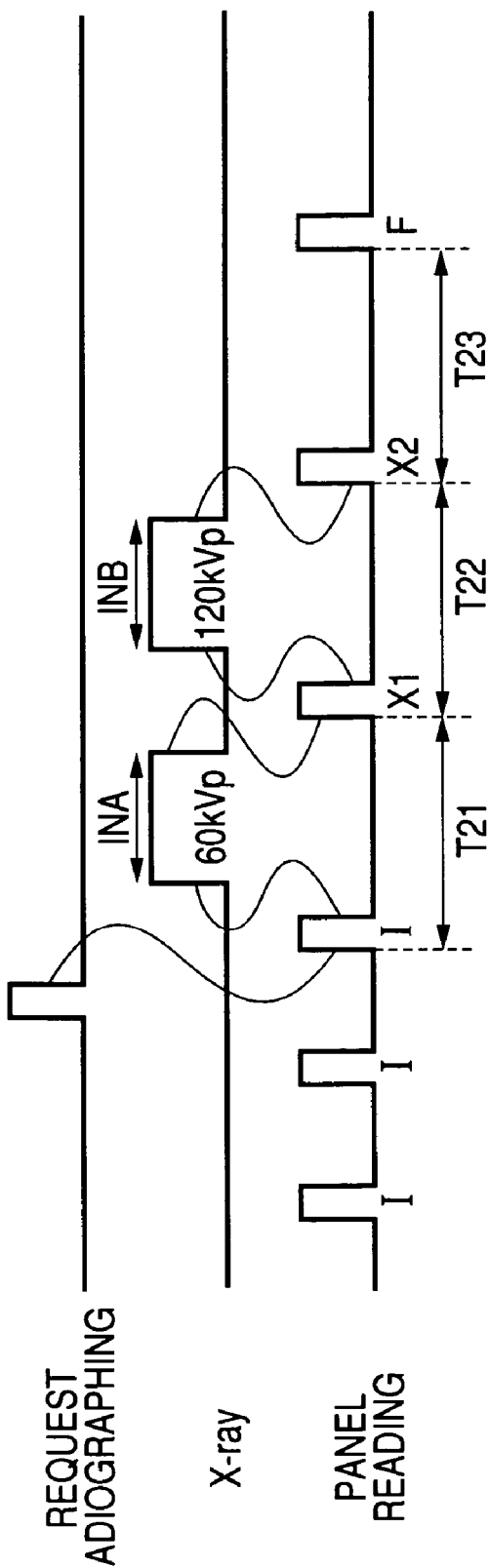

IMAGING APPARATUS AND IMAGING SYSTEM

BACKGROUND OF THE INVENTION

1. Field of the Invention

The present invention relates to an image radiographing (hereinafter, radiographing including not only X-ray radiographing but also photographing for any wavelength range of radiation) apparatus and system, which acquires the corrected output by conducting arithmetic operation processing of a radiographed output and an offset output from an area sensor.

2. Description of the Related Art

Conventionally, an image photographing apparatus or radiographing apparatus employing a sensor array in which photoelectric conversion elements or TFTs formed of amorphous silicon or poly-silicon on a glass substrate are two-dimensionally arranged has been well known. In these apparatuses, it is common that electric charges photoelectrically transferred by photoelectric conversion elements are driven in matrix with TFTs and transferred to a reading device to read them.

An offset correction and driving method for the image radiographing apparatus with the area sensor array was disclosed in Japanese Patent Application Laid-Open No. 2003-244557. FIG. 15 is a diagram showing the system configuration of an X-ray radiographing system to which the conventional image radiographing apparatus is applied. FIG. 16 is a timing chart showing the operation of the X-ray radiographing system as shown in FIG. 15.

As shown in FIG. 15, the X-ray radiographing system comprises an X-ray generator 303, a detection unit 302 for detecting an X-ray passed through a subject 316, a correction unit 308 for performing a correction processing for the data outputted from the detection unit 302, and an output unit 315 such as a monitor for outputting data processed by the correction unit 308. Moreover, it comprises a control unit 301 for controlling the detection unit 302, the X-ray generator 303 and the correction unit 308, a radiographing condition memory 307 accessible by the control unit 301, a radiographing button 305 for issuing a radiographing command to the control unit 301, and a photo timer 304 having an AE (Auto Exposure) function. The detection unit 302 is provided with an area sensor and a reading device (not shown), and the correction unit 308 is provided with an image memory 309 for storing a radiographed output from the detection unit 302, a correction memory 311 for storing an offset output from the detection unit 302 and an arithmetic operation unit 314.

In the conventional X-ray radiographing system constituted in the above way, the area sensor periodically performs a pseudo reading operation (hereinafter referred to as "dummy reading") indicated by "I" in FIG. 16 to reduce the dark current, as shown in FIG. 16. And if the radiographing button 305 is pressed, a radiographing request signal is issued from the radiographing button 305 to the control unit 301. The control unit 301, upon detecting the radiographing request signal, enables the detection unit 301 with the area sensor to perform at least one dummy reading operation. Thereafter, the control unit 301 controls the X-ray generator 303 to start X-ray irradiation. The photo timer 304 having the AE function generates an AE signal (pulse) to the control unit 301 at an appropriate timing during X-ray irradiation. The control unit 301 controls the X-ray generator 303 to stop X-ray irradiation, upon detecting the AE signal (pulse), and stores the charge accumulation time T1 including X-ray irradiation time at this time in the radiographing condition memory 307. Then, the control unit 301 controls the reading device of the detection unit 302 to read the image data from the area sensor. And the output at this time is stored as "radiographed output X" in the image memory 309 within the correction unit 308.

Subsequently, the control unit 301 enables the detection unit 302 to acquire an offset output for correction. That is, the detection unit 302 conducts detection for the charge accumulation time T2 in a state where the X-ray is not irradiated, to read the image data and acquire the offset output F under the radiographing conditions stored in the radiographing condition memory 307. The offset output F is stored in the correction memory 311 within the correction unit 308. At this time, the time T2 is coincident with the X-ray irradiation time T1 stored in the radiographing condition memory 307.

Thereafter, the arithmetic operation unit 314 performs an arithmetic operation processing of "radiographed output X" stored in the image memory 309 and "offset output F" stored in the correction memory 311, and outputs the offset corrected image data to the output unit 315 such as monitor.

Generally, the area sensor made of amorphous silicon used for the conventional image radiographing apparatus is less negligibly affected by the dark current from the photoelectric conversion elements. Accordingly, this method has the great effect in which the X-ray irradiation time T1 is stored in the radiographing condition memory and after the radiographed output is acquired, the offset output is acquired under the condition where the accumulation time T2 is coincident with the X-ray irradiation time T1 as in the above example.

SUMMARY OF THE INVENTION

However, the conventional image radiographing apparatus and X-ray image radiographing system had the following problems. For example, in recent years, it is sought that one apparatus is able to cope with various radiographing modes including still image radiographing, moving image radiographing and energy subtraction owing to the developments of diagnosis engineering and the physical restraints of diagnosis room, but the medical X-ray radiographing apparatus is an independent unit corresponding to each function, such as a still image radiographing dedicated unit and a moving image radiographing dedicated unit. That is, the conventional X-ray image radiographing system is only able to acquire the offset output for correction after acquiring the radiographed output and make the correction, as previously described, and may not cope with various radiographing modes.

Especially in radiographing a heart part of the little child requiring the high speed operation, the time for acquiring the offset output is rate determining, thereby impeding the high speed moving image radiographing in some cases.

Also, the area sensor made of amorphous silicon may be less negligibly affected by the after image. Especially when the moving image with a large contrast and quick motion of the subject is radiographed, the conventional correction method using the offset output after acquiring the radiographed output may be less negligibly affected by the after image.

Moreover, there is a problem that it is not possible to handle a radiographing method of acquiring a plurality of radiographed outputs of different energies successively as occurs with the energy subtraction radiographing.

The present inventors have made careful researches to solve the above-mentioned problems, and conceived various embodiments of the invention as cited below.

It is an object of the present invention to provide an image radiographing apparatus and an image radiographing system, which can easily cope with a plurality of radiographing modes.

The present invention provides an image radiographing apparatus comprising an area sensor, radiographing mode setting means for setting one radiographing mode from among a plurality of radiographing modes that are preset, correction means for performing an arithmetic operation processing using a radiographed output and an offset output from the area sensor, and control means for controlling the operation of the area sensor and the arithmetic operation processing by the correction means in accordance with a signal from the radiographing mode setting means. At least one of the plurality of radiographing modes is an energy subtraction radiographing mode in which the radiographed output of at least two frames acquired by different x-ray energies and the offset output of at least one frame are acquired.

The present invention provides an image radiographing system comprising an X-ray generator, an area sensor, radiographing mode setting means for setting one radiographing mode from among a plurality of radiographing modes that are preset, correction means for performing an arithmetic operation processing using a radiographed output and an offset output from the area sensor, and control means for controlling the operation of the X-ray generator, the operation of the area sensor and the arithmetic operation processing by the correction means in accordance with a signal from the radiographing mode setting means. At least one of the plurality of radiographing modes is an energy subtraction radiographing mode in which the radiographed output of at least two frames acquired by different x-ray energies and the offset output of at least one frame are acquired.

The present invention provides a method for controlling an image radiographing apparatus comprising an area sensor, radiographing mode setting means for setting one radiographing mode from among a plurality of radiographing modes that are preset, and correction means for performing an arithmetic operation processing using a radiographed output and an offset output from the area sensor, the method comprising controlling the operation of the area sensor and the arithmetic operation processing by the correction means in accordance with a signal from the radiographing mode setting means. At least one of the plurality of radiographing modes is an energy subtraction radiographing mode in which the radiographed output of at least two frames acquired by different x-ray energies and the offset output of at least one frame are acquired.

The present invention provides a computer-readable medium encoded with a computer program for controlling an image radiographing apparatus. The image radiographing apparatus comprises an area sensor, radiographing mode setting means for setting one radiographing mode from among a plurality of radiographing modes that are preset, and correction means for conducting an arithmetic operation processing using a radiographed output and an offset output from the area sensor, the program comprising directing the computer to control the operation of the area sensor and the arithmetic operation processing by the correction means in accordance with a signal from the radiographing mode setting means. At least one of the plurality of radiographing modes is an energy subtraction radiographing mode in which the radiographed output of at least two frames acquired by different x-ray energies and the offset output of at least one frame are acquired.

According to the present invention, the correction processing corresponding to the radiographing mode can be conducted. Accordingly, it is possible to easily cope with a plurality of radiographing modes. For example, any one of the still image radiographing mode, moving image radiographing mode, high speed moving image radiographing mode and energy subtraction radiographing mode is selected depending on the contents of correction processing.

BRIEF DESCRIPTION OF THE DRAWINGS

FIG. 12 is a timing chart showing the operation in the first energy subtraction radiographing mode.

DESCRIPTION OF THE PREFERRED EMBODIMENTS

Figure 1:
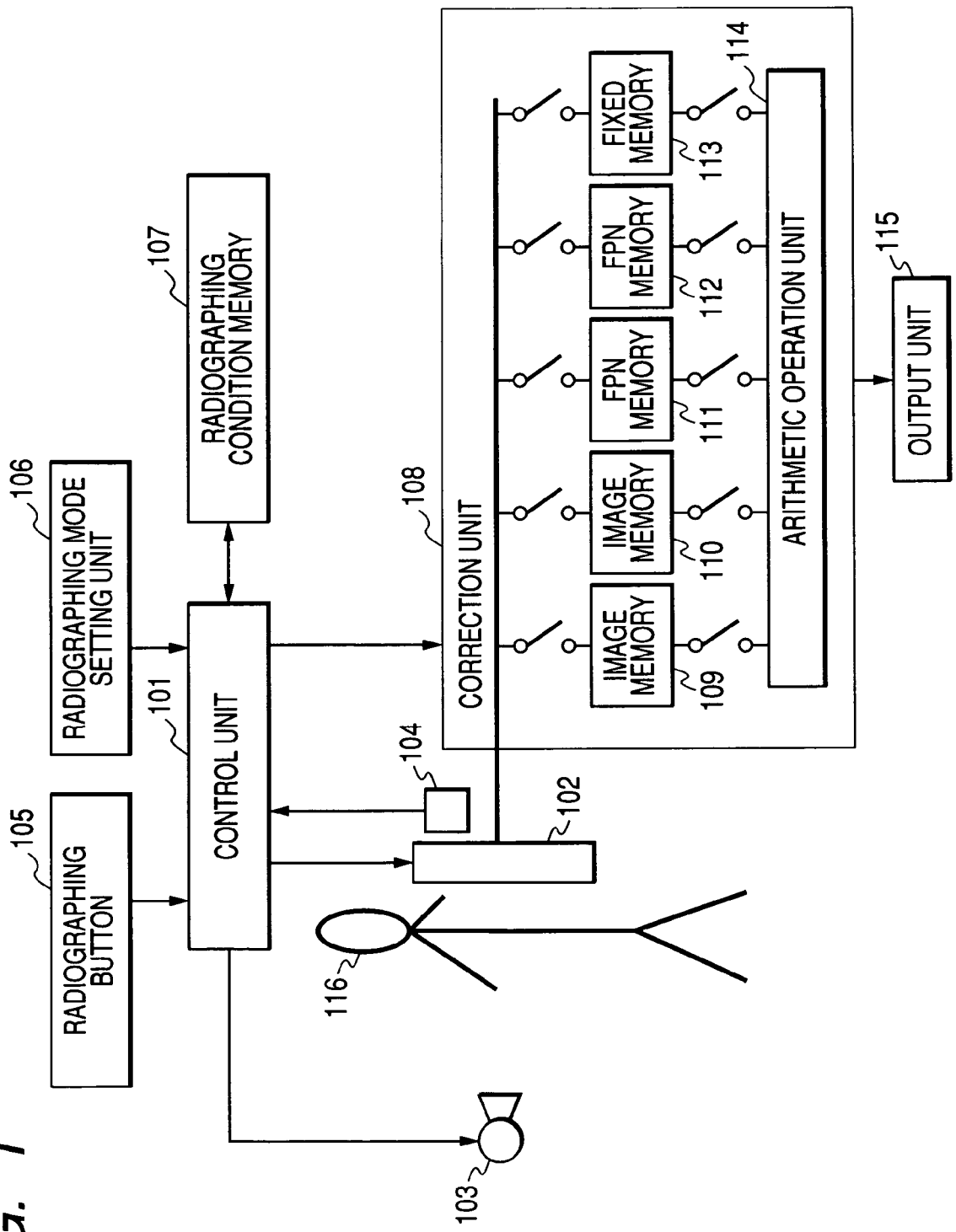
FIG. 1 is a typical diagram showing the configuration of an X-ray image radiographing system according to an embodiment of the present invention.

The preferred embodiments of the present invention will be described below with reference to the accompanying drawings. FIG. 1 is a typical diagram showing the configuration of an X-ray image radiographing system according to an embodiment of the present invention.

In this embodiment, an X-ray image radiographing system comprises an X-ray generator 103, a detection unit 102 for detecting an X-ray passed through a subject 116, a correction unit 108 for performing a correction processing for the data outputted from the detection unit 102, and an output unit 115 such as a monitor for outputting data processed by the correction unit 108, as shown in FIG. 1. Moreover, it comprises a control unit 101 for controlling the detection unit 102, the X-ray generator 103 and the correction unit 108, a radiographing condition memory 107 accessible by the control unit 101, a radiographing button 105 for making a radiographing request to the control unit 101, a radiographing mode setting unit 106 for. setting a radiographing mode in the control unit 101, and a photo timer 104 having an AE (Auto Exposure) function. The radiographing mode setting unit 106 is constituted of a workstation (not shown), for example.

The detection unit 102 is provided with an area sensor array 4 and a reading device 1 (see FIG. 2), and the correction unit 108 is provided with the image memories 109 and 110 for storing a radiographed output from the detection unit 102, the FPN (Fixed Pattern Noise) memories 111 and 112 for storing an offset output from the detection unit 102, and a fixed FPN memory 113 for storing the offset output value Ff for high speed moving image radiographing mode and an arithmetic operation unit 114. When the fixed FPN memory 113 is a ROM, the offset output value for high speed moving image radiographing mode may be stored at the time of product shipment, for example. Also, the average of multiple offset outputs may be stored as the offset output value Ff for the high speed moving image radiographing mode in the fixed FPN memory 113.

Figure 2:
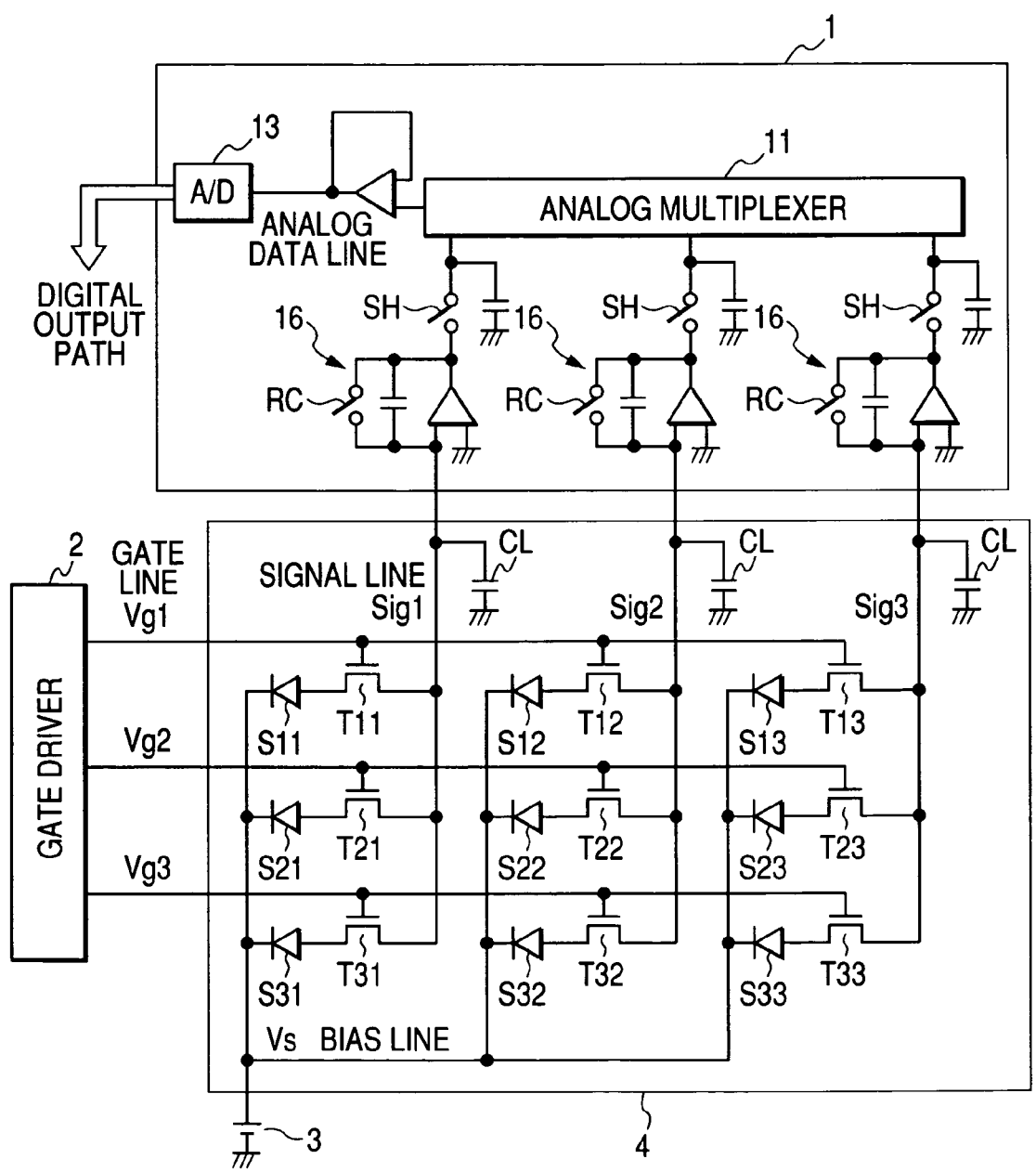
FIG. 2 is a typical circuit diagram showing the circuit configuration of a detection unit 102 in the X-ray image radiographing system according to the embodiment of the invention.

The configuration of the detection unit 102 will be described below. FIG. 2 is a typical circuit diagram showing the circuit configuration of the detection unit 102 in the X-ray image radiographing system according to the embodiment of the invention.

The detection unit 102 is provided with a reading device 1, a gate driver 2, a power source 3 and a sensor array (area sensor) 4, as shown in FIG. 2. The sensor array 4 has an arrangement of pixels composed of the PIN photodiodes S11 to S33 having an amorphous silicon layer and the thin film transistors (TFT) T11 to T33, and is driven in matrix by the gate driver 2. A bias voltage Vs is applied from the power source 3 to a common electrode side of the PIN photodiodes S11 to S33 for the pixels. Also, the gate electrodes of the TFTs T11 to T33 for the pixels are connected to the common gate lines Vg1 to Vg3, which are connected to the gate driver 2 having a shift register (not shown). On the other hand, the source electrodes of the TFTs T11 to T33 are connected to the common signal lines Sig1 to Sig3. The common signal lines Sig1 to Sig3 are connected to the reading device 1.

Within the reading device 1, each of the signal lines Sig1 to Sig3 of the sensor array 4 is connected to a charge-to-voltage conversion amplifier (preamplifier) 16 comprised of an operational amplifier, a feedback capacitor and a reset switch. Moreover, the output side of the charge-to-voltage conversion amplifier 16 is connected via a sample hold switch SH to a sample hold capacitor and an analog multiplexer 11. The analog multiplexer 11 is provided with a switch and a shift register, not shown.

A parallel signal corresponding to plural signal lines Sig1 to Sig3 is converted into a serial signal by the analog multiplexer 11, and outputted to an analog data line. An operational amplifier is connected to this analog data line. An A/D converter 13 is connected to the output side of the operational amplifier, in which analog data is converted into digital form by the A/D converter 13 in synchronism with a clock signal AD_CLK, and digital data after conversion is outputted to a digital output Busconforming to the resolution of the A/D converter 13.

Figure 3:
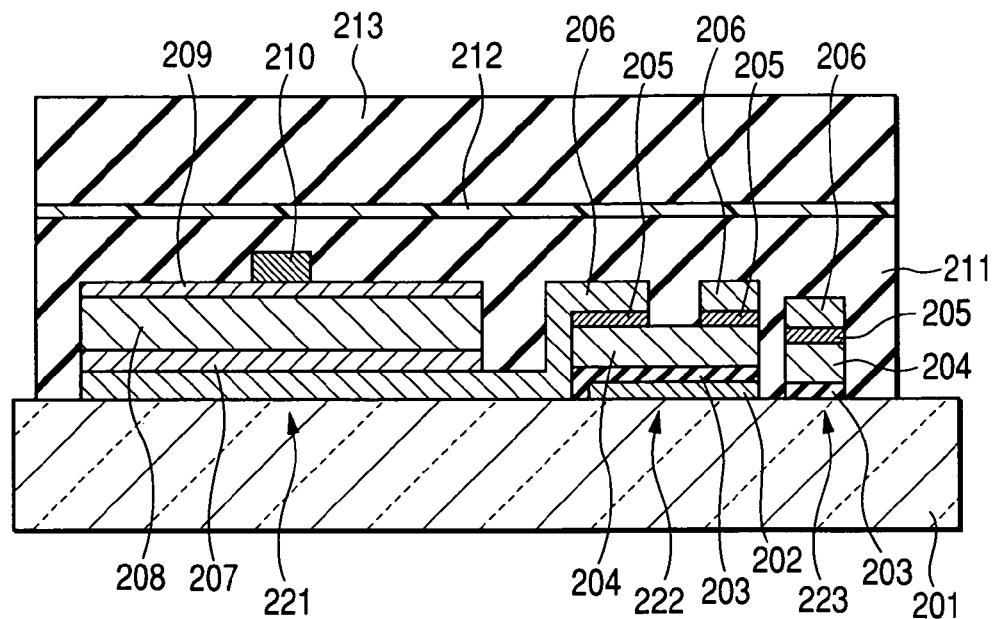
FIG. 3 is a cross-sectional view showing a pixel of a sensor array.

A cross-sectional structure of the pixel of the sensor array will be described below. FIG. 3 is a cross-sectional view showing the pixel of the sensor array.

At each pixel, a thin film transistor (TFT) 222 for selection is constituted in which a gate electrode layer (lower electrode) 202, an insulating layer (amorphous silicon nitride film) 203, an amorphous silicon semiconductor layer 204, an n-type amorphous silicon layer 205 and a source-drain electrode layer (upper electrode layer) 206 are laminated on a glass substrate 201. Also, a photodiode 221 is constituted in which a portion (lower electrode layer) extended from the source-drain electrode layer 206, a p-type amorphous silicon layer 207, an amorphous silicon semiconductor layer 208, an n-type amorphous silicon layer 209 and an upper electrode layer 210 are laminated on the glass substrate. Moreover, a wiring portion 223 is constituted in which the insulating layer 203, the amorphous silicon semiconductor layer 204, the n-type amorphous silicon layer 205 and the source-drain electrode layer 206 are laminated on the glass substrate 201. Moreover, a protective layer 211 composed of amorphous silicon nitride film covering them is formed, and a scintillator layer 213 is bonded thereon by an adhesive layer 212.

Note that the scintillator layer 213 is provided to convert the radioactive ray (X-ray) into the visible ray. Generally, the photodiode constituted of amorphous silicon is very insensitive to the X-ray. The scintillator layer 213 is made of gadolinium based material or CsI (cesium iodide).

In the detection unit 102 of such a photoelectric transfer device (X-ray image pick-up device), X-rays passed through the subject are incident upon the scintillator layer, and converted into visible rays. And visible rays are incident upon the photodiode. In the photodiode, electric charges are generated in the semiconductor layer, and if TFT is turned on, charges are sequentially transferred to the reading circuit to read them.

Figure 4:
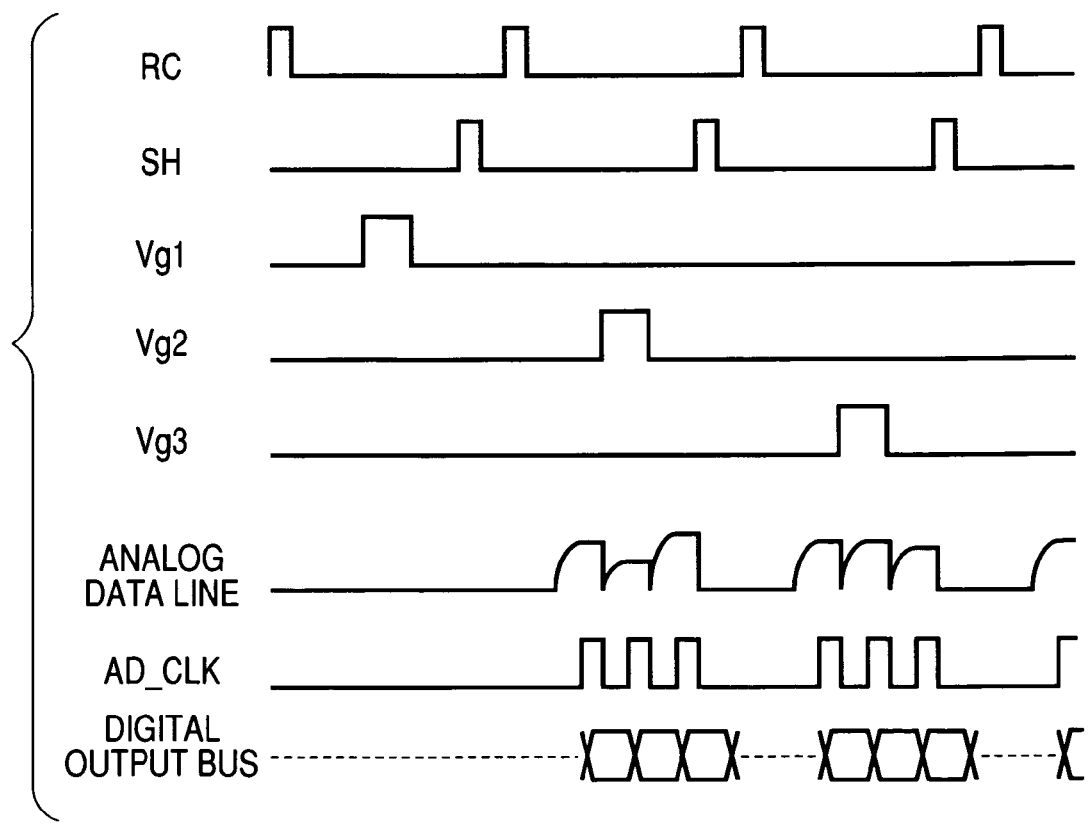
FIG. 4 is a timing chart showing the operation of the detection unit 102.

The operation of the detection unit 102 will be described below. FIG. 4 is a timing chart showing the operation of the detection unit 102.

First of all, the preamplifier 16 and each common signal line are reset upon a reset signal RC from a timing generator (not shown). Then, if a pulse is applied to a common gate line Vg1, the TFTs T11 to T13 connected to the common gate line Vg1 are turned on, so that signal charges generated in the photodiodes S11 to S13 are transferred via the common signal lines Sig1 to Sig3 to the reading device 1. The transferred charges are converted into voltage by the preamplifier 16. Then, when a sample hold signal SH is applied from the timing generator (not shown) to the reading device 1, a voltage output from the preamplifier 16 is sampled into a sample hold capacitor.

Thereafter, the voltage sampled into the sample hold capacitor is serially converted by the analog multiplexer 11 and outputted to the analog data line. A serial analog signal outputted to the analog data line is inputted into the A/D converter 13, and converted into digital signal by the A/D converter 13 in synchronism with a clock signal AD_CLK, the converted digital signal being outputted to the digital output Busconforming to the resolution of the A/D converter 13. In a case where the X-ray image radiographing system is employed as the medical X-ray radiographing system, the resolution of the A/D converter is preferably 14 bit or more.

The above operation is repeated for the signal lines Vg2 and Vg3, until reading from the entire sensor array 4 is completed. Note that the radioactive ray (or X-ray) is either continuous light (or continuous X-ray) or pulsed light (or pulsed X-ray).

The X-ray image radiographing system constituted in the above way is able to conduct (1) the operation in a still image radiographing mode (acquiring the offset output after acquiring the radiographed output), (2) the operation in a moving image radiographing mode (acquiring the offset output immediately after or before acquiring the radiographed output), (3) the operation in a high speed moving image radiographing mode (without acquiring the offset output every time of acquiring the radiographed output) and (4) the operation in an energy subtraction radiographing mode. Operating the radiographing mode setting unit 106 makes the switching between these modes.

The operation of the X-ray image radiographing system according to the embodiment of the present invention will be described for each of the above modes.

(Still Image Radiographing Mode)

Figure 5:
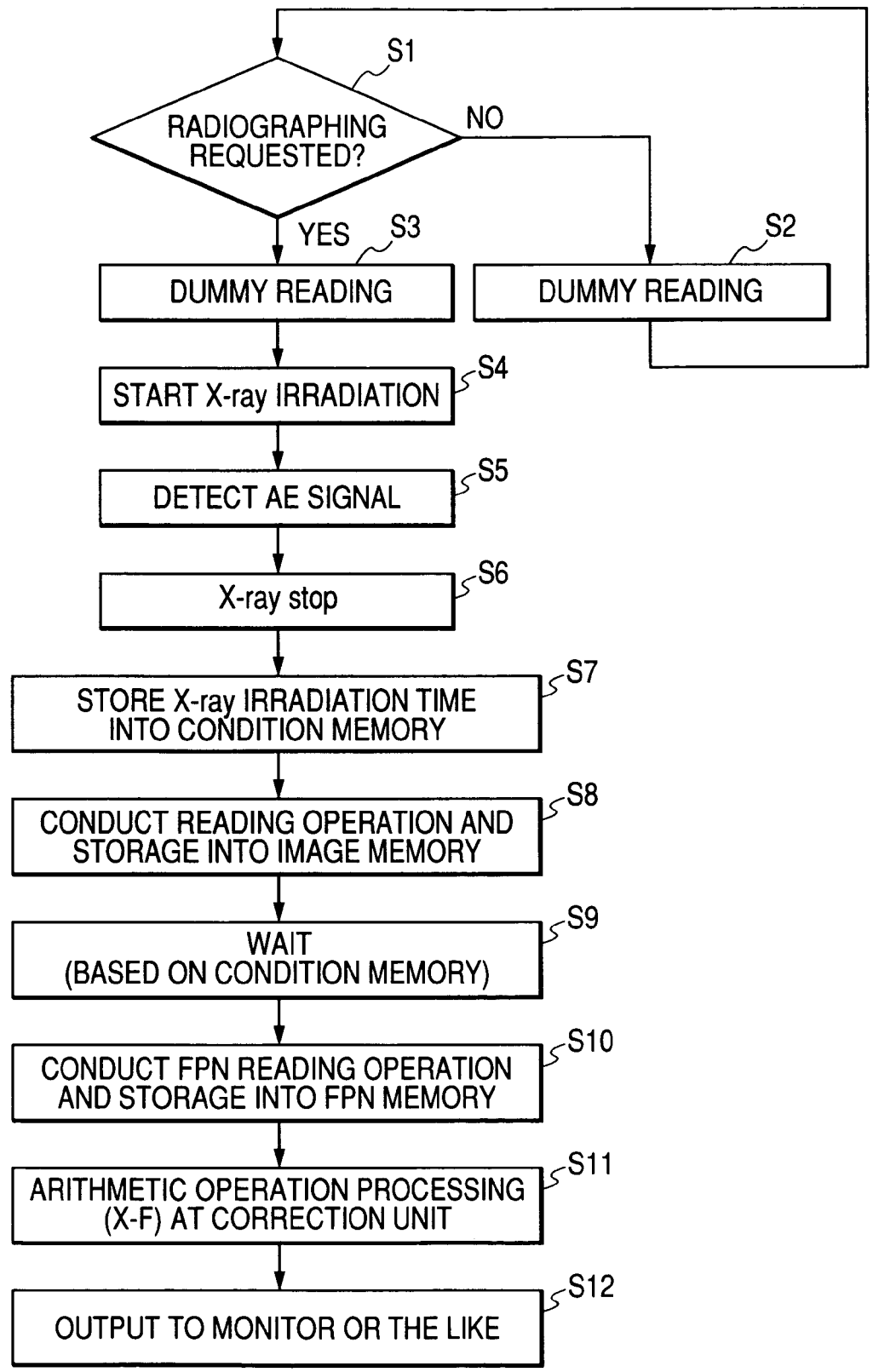
FIG. 5 is a flowchart showing the operation in a still image radiographing mode.
Figure 6:
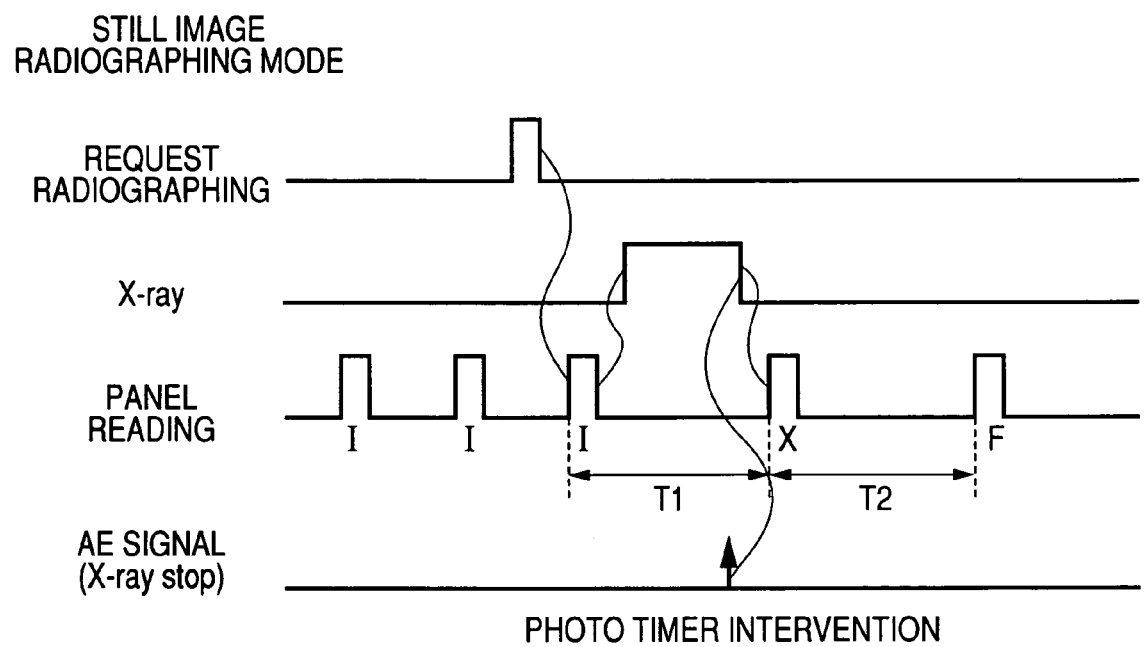
FIG. 6 is a timing chart showing the operation in the still image radiographing mode.

First of all, the operation in the still image radiographing mode will be described. FIG. 5 is a flowchart showing the operation in the still image radiographing mode. FIG. 6 is a timing chart showing the operation in the still image radiographing mode.

If the still image radiographing mode is selected by the radiographing mode setting unit 106 constituted of a workstation and so on, the radiographing button 105 for requesting the X-ray irradiation becomes active to determine whether or not radiographing is requested (step S1). If there is no radiographing request, the control unit 101 periodically conducts the dummy reading operation as indicated by "I" in FIG. 6 to reduce the dark current (step S2).

And if the radiographing button 105 is pressed, a radiographing request signal is outputted from the radiographing button 105 to the control unit 101. The control unit 101, upon detecting the radiographing request signal, enables the detection unit 102 having the area sensor array 4 to conduct at least one dummy reading operation (step S3). Thereafter, the control unit 101 controls the X-ray generator 103 to start X-ray irradiation (step S4). The photo timer 104 having the AE function generates an AE signal (pulse) to the control unit 101 at an appropriate timing during X-ray irradiation. If the control unit 101 detects the AE signal (pulse) (step S5), it enables the X-ray generator 103 to stop X-ray irradiation (step S6), and the sensor accumulation time T1 including X-ray irradiation time at this time is stored in the radiographing condition memory 107 (step S7). Then, the control unit 101 enables the reading device 1 to conduct the reading operation from the area sensor array 4 and storage of read data as "radiographed output X" into the image memory 109 within the correction unit 108 (step S8). Herein, the sensor accumulation time T1 is the time from the start of the final dummy reading operation I till the start of the reading operation X.

Subsequently, the control unit 101 enables the detection unit 102 to acquire an offset output for correction in the still image radiographing mode. That is, the detection unit 102 conducts detection for the sensor accumulation time T2 in a state where the X-ray is not irradiated under the radiographing conditions stored in the radiographing condition memory 107 (step S9) to read the image data and acquire the offset output F. The offset output F is stored in the FPN memory 111 within the correction unit 108 (step S10). At this time, the sensor accumulation time T2 is coincident with the sensor accumulation time T1 including X-ray irradiation time stored in the radiographing condition memory 107.

Thereafter, the arithmetic operation unit 114 conducts arithmetic operation processing for "radiographed output X" stored in the image memory 109 and "offset output F" stored in the FPN memory 111 for correction (step S11), and outputs the offset corrected image data to the output unit 115 such as monitor (step S12). The arithmetic operation unit 114 obtains the corrected output by conducting arithmetic operation processing of "radiographed output X−offset output F", for example.

(Moving Image Radiographing Mode)

Figure 7:
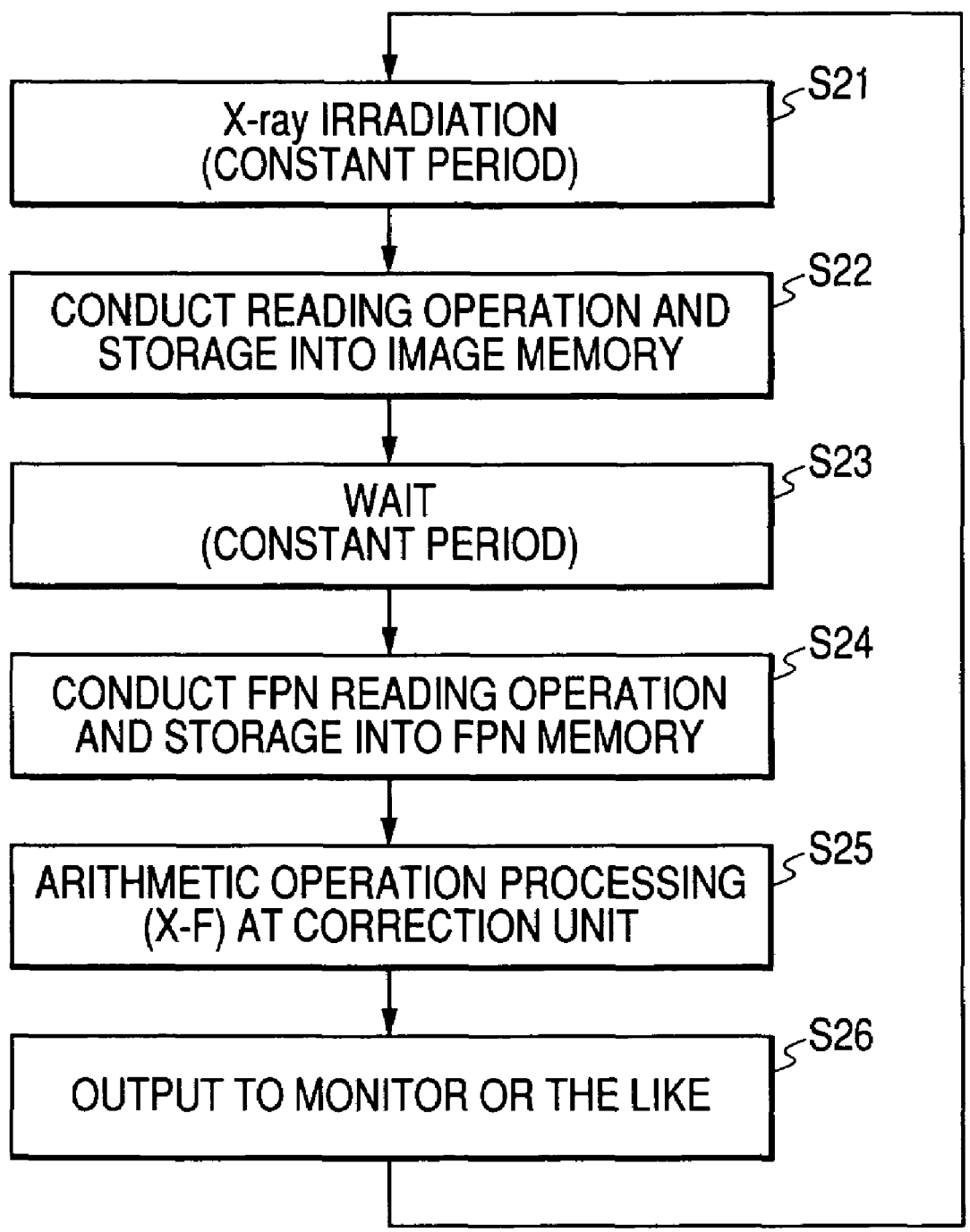
FIG. 7 is a flowchart showing the operation in a moving image radiographing mode.
Figure 8:
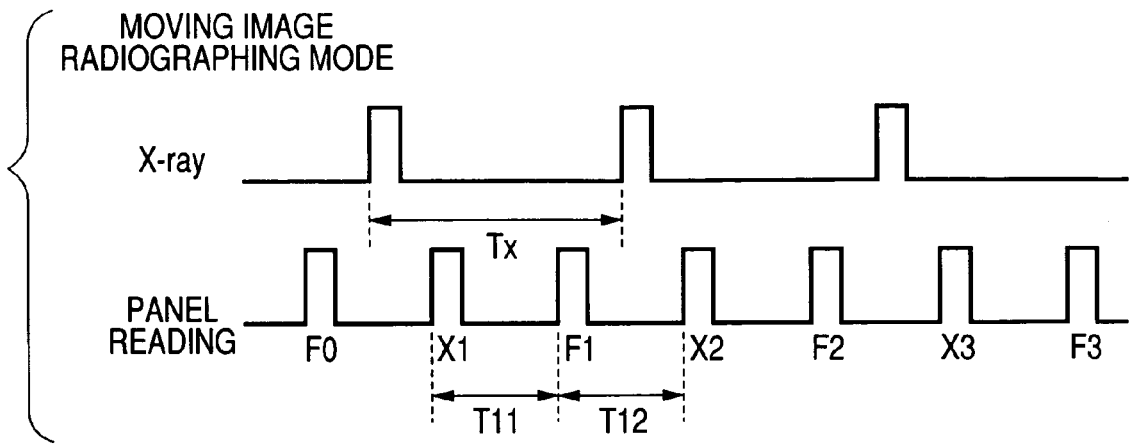
FIG. 8 is a timing chart showing the operation in the moving image radiographing mode.

The operation in the moving image radiographing mode will be described below. FIG. 7 is a flowchart showing the operation in the moving image radiographing mode, and FIG. 8 is a timing chart showing the operation in the moving image radiographing mode.

If the moving image radiographing mode is selected by the radiographing mode setting unit 106, the moving image radiographing is started, irrespective of whether or not the radiographing button 105 for requesting the X-ray irradiation is pressed.

That is, the control unit 101 firstly controls the X-ray generator 103 to conduct X-ray irradiation at predetermined period Tx (step S21). Also, the control unit 101 controls the detection unit 102 so that the reading device 1 conducts the reading operation (Xn (n=1, 2, . . . )) from the area sensor array 4 for a period from one X-ray irradiation to the next X-ray irradiation and storage of read data as "radiographed output Xn" into the image memory 109 within the correction unit 108 (step S22). Moreover, after a predetermined sensor accumulation time (interval) T11 has passed from the reading operation (step S23), the control unit 101 enables the reading device 1 to conduct the reading operation (Fn) from the area sensor array 4 and storage of offset output Fn into the FPN memory 111 within the correction unit 108 (step S24). And after the predetermined sensor accumulation time (interval) T12 has passed, the reading operation of Xn is conducted again. Note that the control unit 101 enables the reading device 1 to conduct the reading operation (Xn) and (Fn) for a period from one X-ray irradiation to the next X-ray irradiation.

Herein, there is desirably the following relationship between the X-ray irradiation period Tx and the sensor accumulation time (interval) T11 and T12 for reading.

$Tx=T11+T12$

Or $T11=T12$ and $Tx=k \cdot T11$ ($k$ is constant)

Thereafter, the arithmetic operation unit 114 conducts arithmetic operation processing for "radiographed output Xn" stored in the image memory 109 and "offset output Fn" stored in the FPN memory 111 for correction (step S25), and outputs the offset corrected image data to the output unit 115 such as monitor (step S26). The arithmetic operation unit 114 obtains the corrected output by conducting arithmetic operation processing of "radiographed output Xn−offset output Fn", for example.

When the subject has a large contrast and moves fast and is significantly affected by the after image, the control unit 101 may control the correction unit 108 in the following way. That is, it may control the correction unit 108 to store the offset output F(n−1) immediately before acquiring the radiographed output Xn in the FPN memory 112, and the arithmetic operation unit 114 to conduct arithmetic operation processing of "Xn−F(n−1)".

Figure 9:
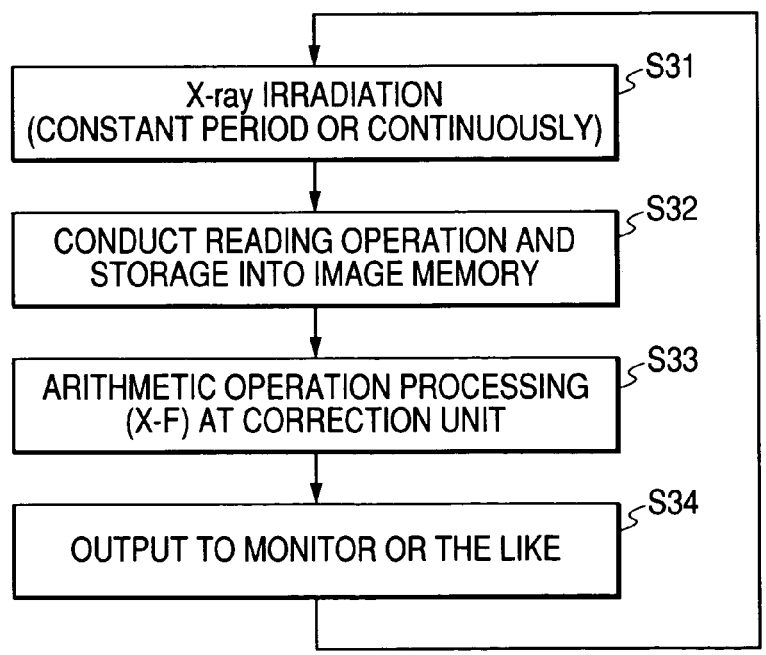
FIG. 9 is a flowchart showing the operation in a high speed moving image radiographing mode.
Figure 10:
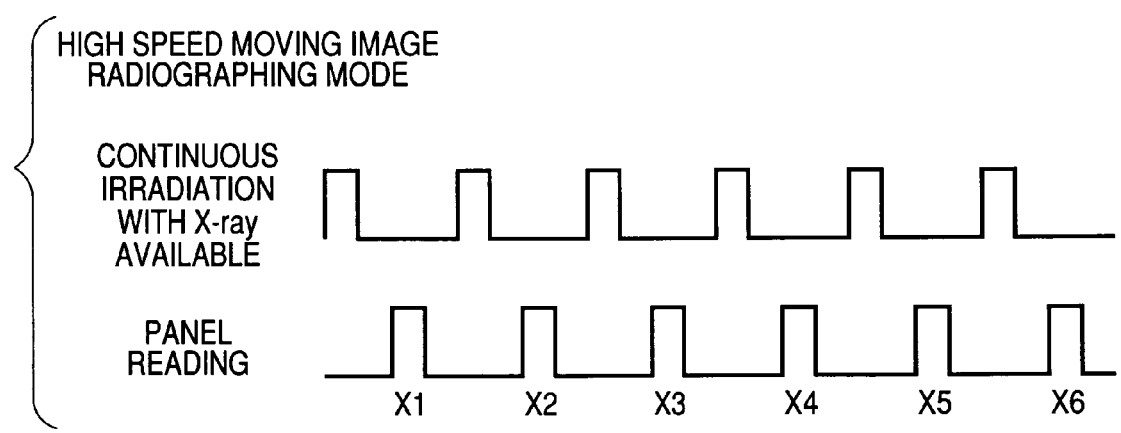
FIG. 10 is a timing chart showing the operation in the high speed moving image radiographing mode.

The operation in the high speed moving image radiographing mode will be described below. The high speed moving image radiographing mode is the mode suitable for radiographing a heart part of the little child. FIG. 9 is a flowchart showing the operation in the high speed moving image radiographing mode, and FIG. 10 is a timing chart showing the operation in the high speed moving image radiographing mode.

If the high speed moving image radiographing mode is selected by the radiographing mode setting unit 106, the high speed moving image radiographing is started, irrespective of whether or not the radiographing button 105 for requesting the X-ray irradiation is pressed.

That is, the control unit 101 firstly controls the X-ray generator 103 -to conduct X-ray irradiation at predetermined period Tx (step S31). In the case where the correction is made employing the fixed offset output as in this mode, the X-ray irradiation may be continuous. Also, the control unit 101 controls the detection unit 102 so that the reading device 1 conducts the reading operation (Xn (n=1, 2, ... )) from the area sensor array 4 for a period from one X-ray irradiation to the next X-ray irradiation and storage of read data as "radiographed output Xn" into the image memory 109 within the correction unit 108 (step S32).

Thereafter, the arithmetic operation unit 114 conducts arithmetic operation processing for "radiographed output Xn" stored in the image memory 109 and "fixed offset output value Ff" stored in the fixed FPN memory 113 (step S33), and outputs the offset corrected image data to the output unit 115 such as monitor (step S34). The arithmetic operation unit 114 obtains the corrected output by conducting arithmetic operation processing of "radiographed output Xn−fixed offset output value Ff", for example. Note that the fixed offset output value Ff may be set up at the time of product shipment, as previously described, but is preferably the average of plural offset outputs from the viewpoint of reducing the noise.

In this way, in the high speed moving image radiographing mode, unlike the moving image radiographing mode, the offset output is not acquired, whereby high speed radiographing is achieved.

(Energy Subtraction Radiographing Mode)

Figure 11:
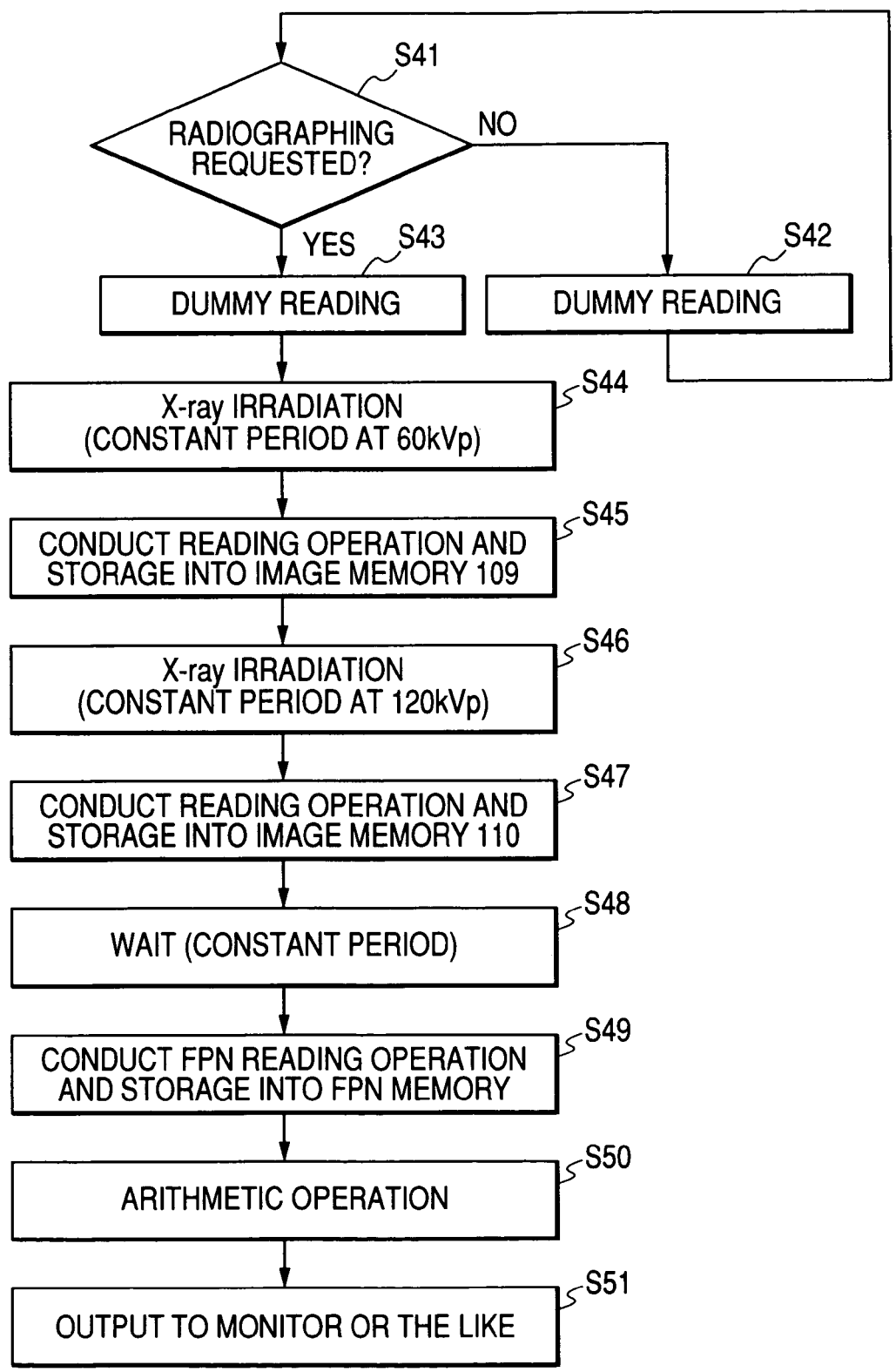
FIG. 11 is a flowchart showing the operation in a first energy subtraction radiographing mode.

The operation in the energy subtraction radiographing mode will be described. In this embodiment, two kinds of energy subtraction radiographing mode are set up. FIG. 11 is a flowchart showing the operation in the first energy subtraction radiographing mode. FIG. 12 is a timing chart showing the operation in the first energy subtraction radiographing mode.

If the first energy subtraction radiographing mode is selected by the radiographing mode setting unit 106, the radiographing button 105 for requesting the X-ray irradiation becomes active to determine whether or not radiographing is requested (step S41). If there is no radiographing request, the control unit 101 periodically conducts the dummy reading operation as indicated by "I" in FIG. 12 to reduce the dark current (step S42).

And if the radiographing button 105 is pressed, a radiographing request signal is outputted from the radiographing button 105 to the control unit 101. The control unit 101, upon detecting the radiographing request signal, enables the detection unit 102 having the area sensor array to conduct at least one dummy reading operation (step S43).

Thereafter, the control unit 101 controls the X-ray generator 103 to conduct the first X-ray irradiation (step S44). The first X-ray irradiation is conducted at a preset energy (e.g., 60 kVp) and for a preset time INA. Then, the control unit 101 enables the reading device 1 to conduct the reading operation from the area sensor array 4 and storage of read data as "radiographed output X1" into the image memory 109 within the correction unit 108 (step S45). At this time, there is the relationship T21>INA between the sensor accumulation time T21 and the X-ray irradiation time INA under the timing control.

Subsequently, the control unit 101 controls the X-ray generator 103 to conduct the second X-ray irradiation (step S46). The energy of the second X-ray irradiation is different from that of the first X-ray irradiation. The second X-ray irradiation is conducted at a preset energy (e.g., 120 kVp) and for a preset time INB. Then, the control unit 101 enables the reading device 1 to conduct the reading operation from the area sensor array 4 and storage of read data as "radiographed output X2" into the image memory 110 within the correction unit 108 (step S47) ., At this time, there is the relationship T22>INB between the sensor accumulation time T22 and the X-ray irradiation time INB and the relationship T21=T22 between the sensor accumulation time T21 and the sensor accumulation time T22 under the timing control. Herein, the X-ray irradiation times INA and INB may be different from each other.

Then, the control unit 101 enables the detection unit 102 to acquire the offset output for correction. That is, the detection unit 102 conducts detection only for the preset sensor accumulation time T23 (step S48) to read the image data and acquire the offset output F1. The offset output F1 is stored in the FPN memory 111 within the correction unit 108 (step S49). At this time, the sensor accumulation time T23 is coincident with the sensor accumulation time T21 (=T22).

Thereafter, the arithmetic operation unit 114 conducts arithmetic operation processing for "radiographed output X1" stored in the image memory 109, "radiographed output X2" stored in the image memory 110 and "offset output F1" stored in the FPN memory 111 for correction (step S50), generates the image data for energy subtraction from these data, and outputs this image data to the output unit 115 such as monitor (step S51). The arithmetic operation unit 114 conducts arithmetic operation processings of "radiographed output X1−offset output F1" and "radiographed output X2−offset output", for example.

In this way, in the first energy subtraction radiographing mode, two radiographed outputs X1 and X2 are corrected employing the same offset output F1.

Figure 13A:
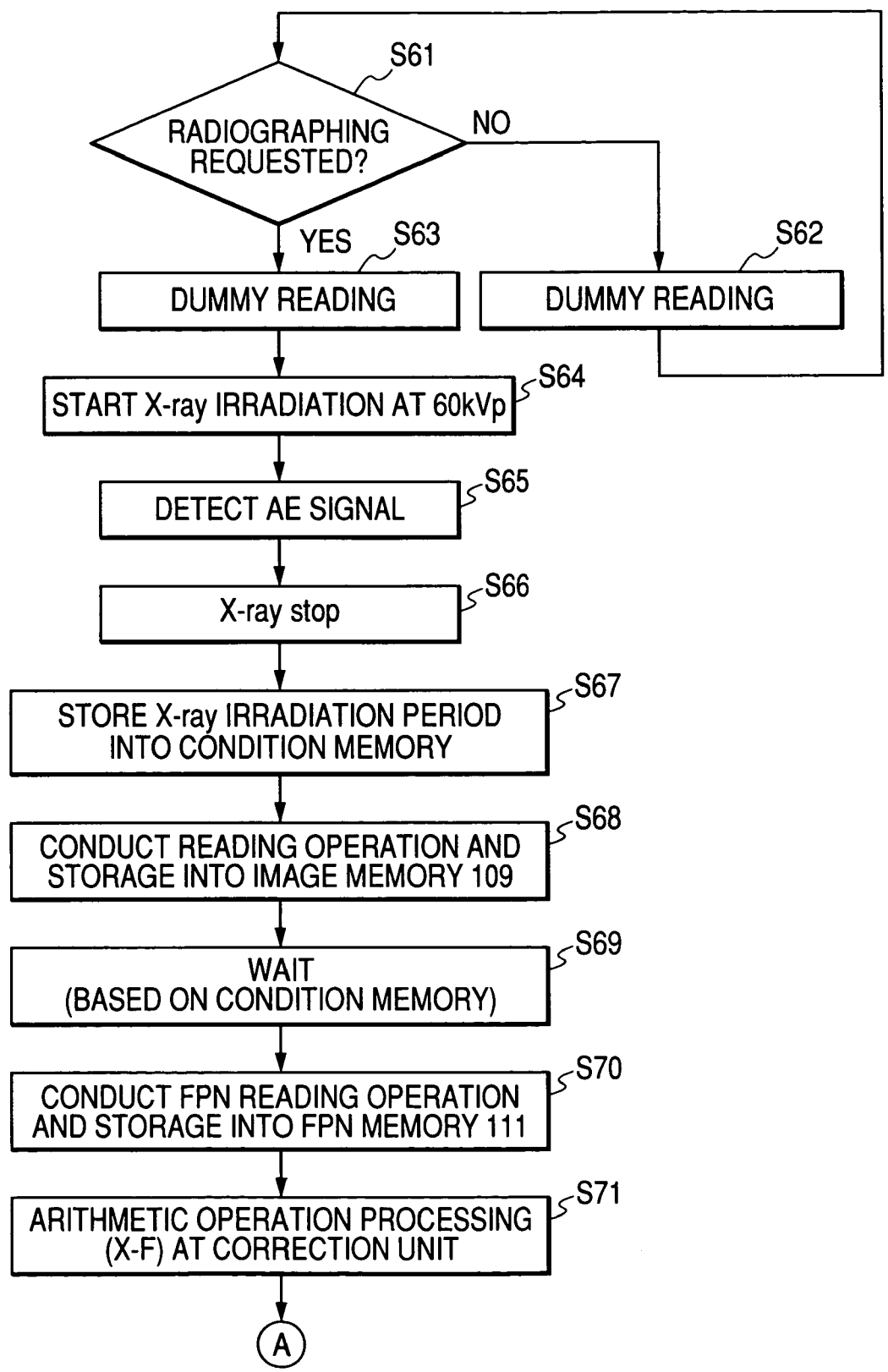
FIG. 13A is a flowchart showing the operation in a second energy subtraction radiographing mode.
Figure 13B:
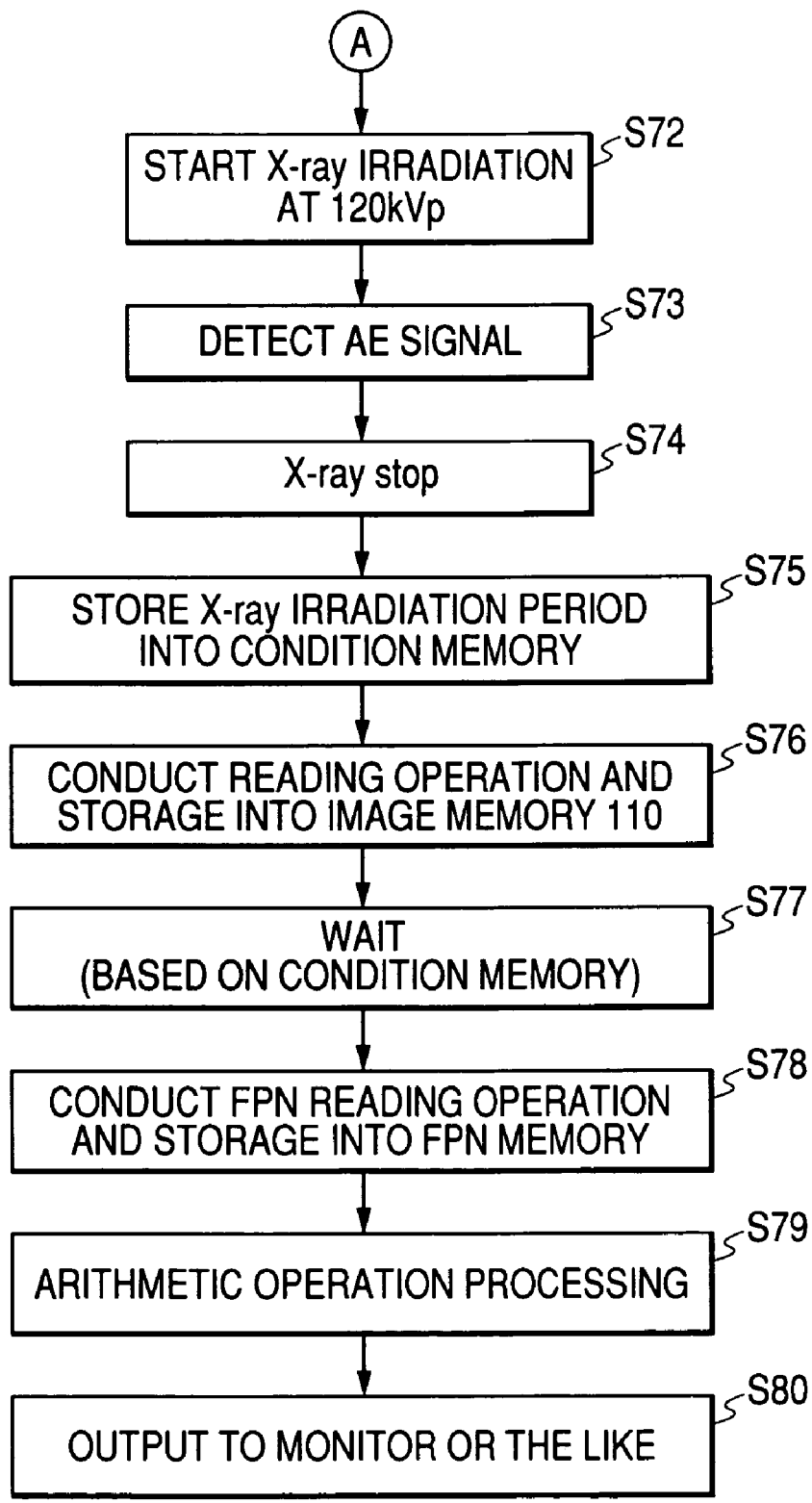
FIG. 13B is a flowchart showing the operation in the second energy subtraction radiographing mode, continued from FIG. 13A.
Figure 14:
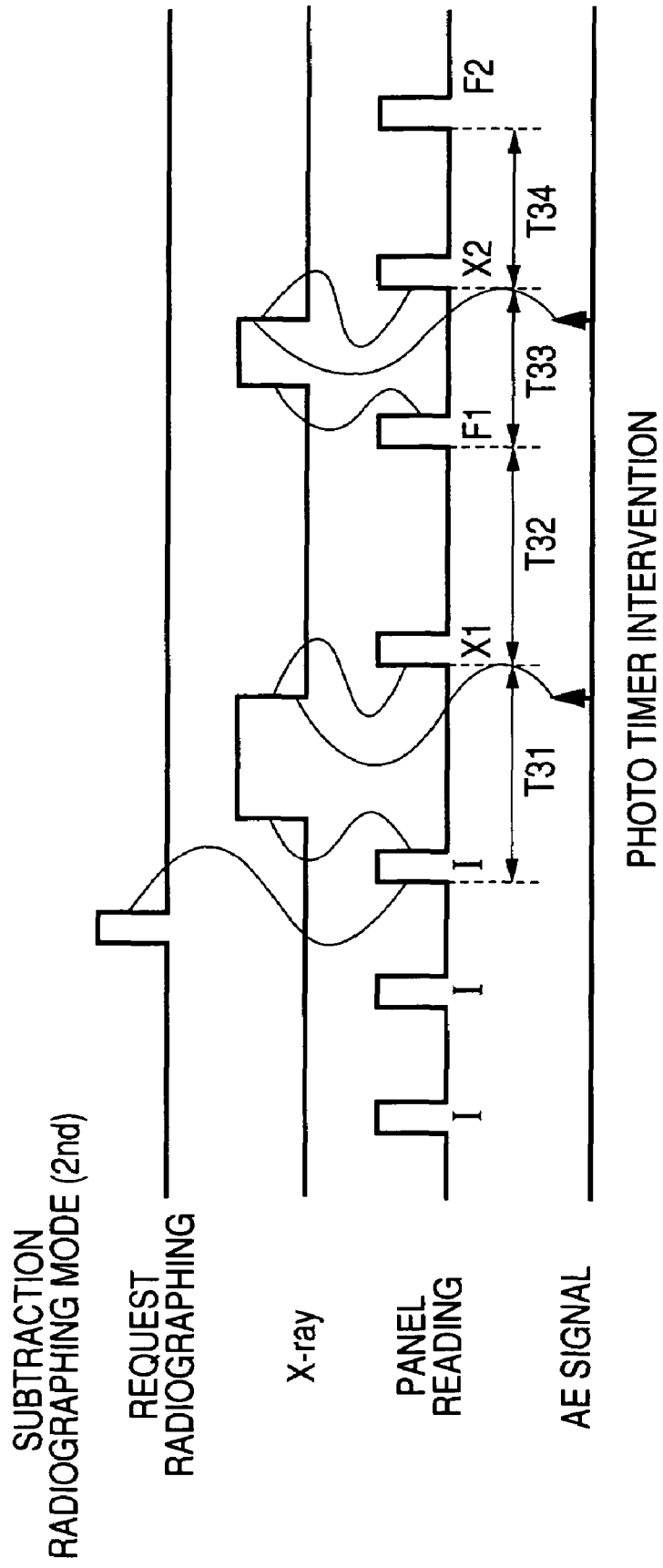
FIG. 14 is a timing chart showing the operation in the second energy subtraction radiographing mode.
Figure 15:
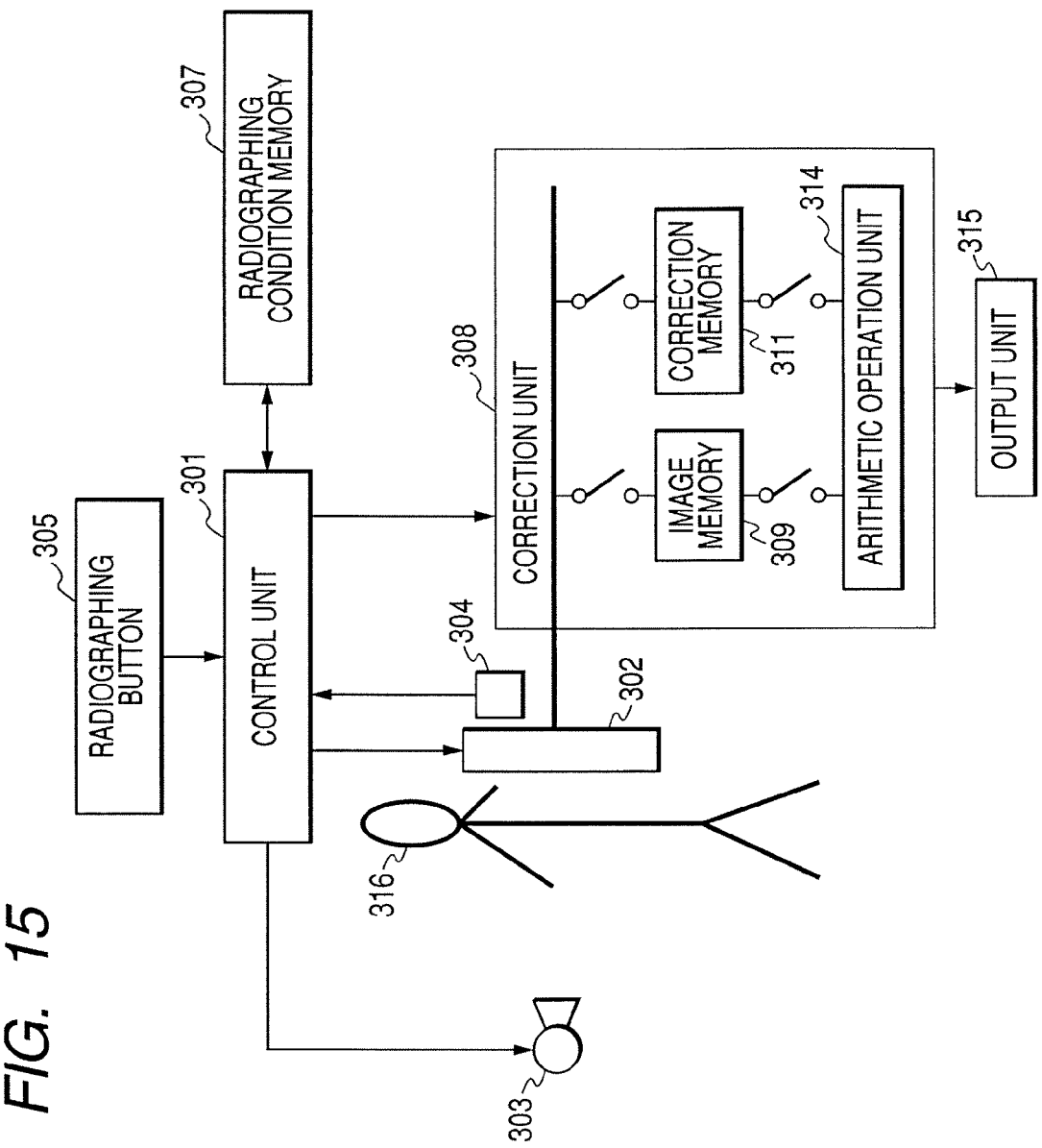
FIG. 15 is a diagram showing the system configuration of an X-ray radiographing system to which the conventional image radiographing apparatus is applied.
Figure 16:
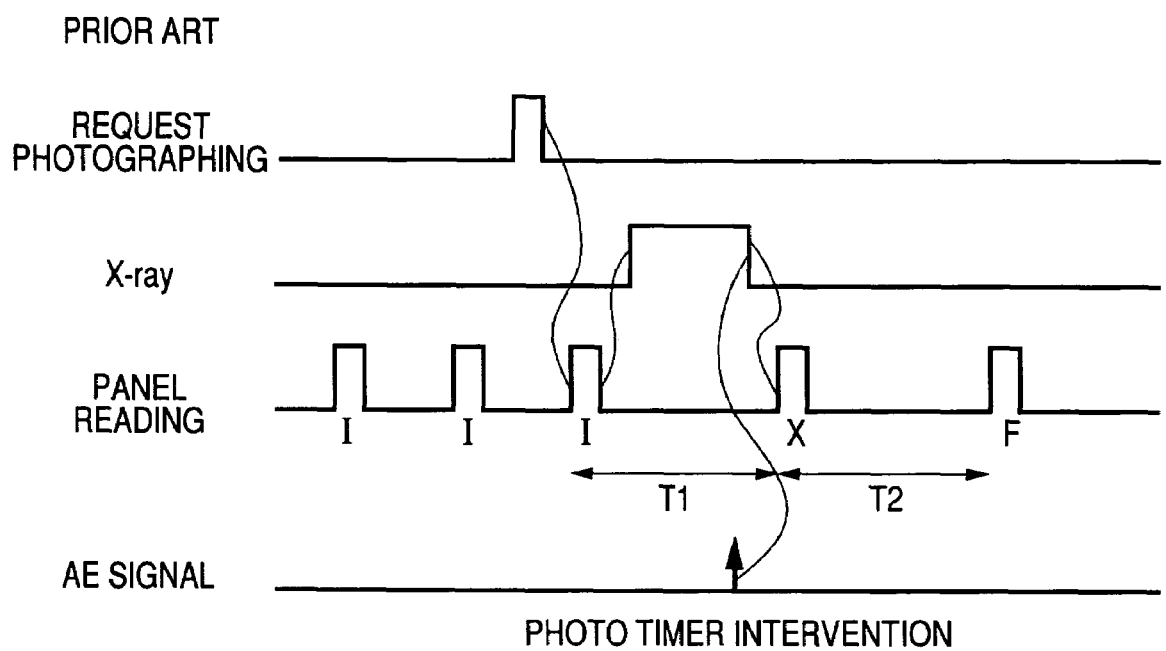
FIG. 16 is a timing chart showing the operation of the X-ray radiographing system as shown in FIG. 15.

FIGS. 13A and 13B are flowcharts showing the operation in the second energy subtraction radiographing mode. FIG. 14 is a timing chart showing the operation in the second energy subtraction radiographing mode.

If the second energy subtraction radiographing mode is selected by the radiographing mode setting unit 106, the radiographing button 105 for requesting the X-ray irradiation becomes active to determine whether or not radiographing is requested (step S61). If there is no radiographing request, the control unit 101 periodically conducts the dummy reading operation as indicated by "I" in FIG. 14 to reduce the dark current (step S62).

And if the radiographing button 105 is pressed, a radiographing request signal is outputted from the radiographing button 105 to the control unit 101. The control unit 101, upon detecting the radiographing request signal, enables the detection unit 102 having the area sensor array 4 to conduct at least one dummy reading operation (step S63). Thereafter, the control unit 101 controls the X-ray generator 103 to start the first X-ray irradiation (step S64). The first X-ray irradiation is conducted at a preset energy (e.g., 60 kVp) . The photo timer 104 having the AE function generates an AE signal (pulse) to the control unit 101 at an appropriate timing during X-ray irradiation. The control unit 101 detects the AE signal (pulse) (step S65), and then controls the X-ray generator 103 to stop X-ray irradiation (step S66), and stores the sensor accumulation time T31 including X-ray irradiation time at this time in the radiographing condition memory 107 (step S67). Then, the control unit 101 enables the reading device 1 to conduct the reading operation from the area sensor array 4 and storage of read data as "radiographed output X1" into the image memory 109 within the correction unit 108 (step S68).

Subsequently, the control unit 101 enables the detection unit 102 to acquire the offset output for correction. That is, the detection unit 102 conducts detection only for the sensor accumulation time T32 in a state where the X-ray is not irradiated under the radiographing conditions stored in the radiographing condition memory 107 (step S69) to read the image data and acquire the offset output F1. The offset output F1 is stored in the FPN memory 111 within the correction unit 108 (step S70). At this time, the sensor accumulation time T32 is coincident with the sensor accumulation time T31 including the X-ray irradiation time stored in the radiographing condition memory 107.

Thereafter, the arithmetic operation unit 114 conducts arithmetic operation processing of "radiographed output X1" stored in the image memory 109 and "offset output F1" stored in the FPN memory 111 for correction (step S71). The arithmetic operation unit 114 conducts arithmetic operation processing of "radiographed output X−offset output F1", for example.

Subsequently, the control unit 101 controls the X-ray generator 103 to conduct the second X-ray irradiation (step S72). The energy of the second X-ray irradiation is different from that of the first X-ray irradiation. The second X-ray irradiation is conducted at a preset energy (e.g., 120 kVp). The photo timer 104 generates an AE signal (pulse) to the control unit 101 at an appropriate timing during X-ray irradiation. The control unit 101 detects the AE signal (pulse) (step S73), and then controls the X-ray generator 103 to stop X-ray irradiation (step S74), and stores the sensor accumulation time T33 including X-ray irradiation time at this time in the radiographing condition memory 107 (step S75) Then, the control unit 101 enables the reading device 1 to conduct the reading operation from the area sensor array 4 and storage of read data as "radiographed output X2" into the image memory 110 within the correction unit 108 (step S76).

Then, the control unit 101 enables the detection unit 102 to acquire the offset output for correction. That is, the detection unit 102 conducts detection only for the preset sensor accumulation time T34 (step S77) to read the image data and acquire the offset output F2. The offset output F2 is stored in the FPN memory 112 within the correction unit 108 (step S78). At this time, the sensor accumulation time T34 is coincident with the sensor accumulation time T33 including the X-ray irradiation time stored in the radiographing condition memory 107.

Thereafter, the arithmetic operation unit 114 conducts arithmetic operation processing of "radiographed output X2" stored in the image memory 109 and "offset output F2" stored in the FPN memory 112 for correction (step S79). The arithmetic operation unit 114 conducts arithmetic operation processing of "radiographed output X2−offset output F2", for example. And the image data for energy subtraction is generated from each data obtained at steps S71 and S79, and outputted to the output unit 115 such as monitor (step S80).

In this way, the radiographing mode setting unit 106 connected to the control unit 101 is provided in this embodiment. Also, the correction unit 108 is provided with a plurality of frame memories 109 to 113 to allow for multiple offset correction methods. Accordingly, the control unit 101 controls the correction unit 108 to select one arithmetic operation processing from among the plural arithmetic operation processings (correction methods) in accordance with the radiographing mode.

In the above embodiment, for convenience sake of explanation, the correction unit 108 is provided with five memories, but a smaller number of memories may be preferably employed. Also, when the photoelectric conversion element has an MIS sensor, it is preferred that the refresh operation is performed before each reading operation. Also, it is preferred that means for deciding the offset correction method is provided separately. For example, means for detecting a contrast threshold value of image, storage means for storing a threshold value of moving image radiographing speed and/or a correction method change button are preferably provided. Also, the correction unit may perform, besides the offset correction, the gain correction, energy subtraction image processing, frequency processing, and any other arithmetic operation processing.

Also, the area sensor may be made of amorphous silicon or poly-silicon. The photoelectric conversion element may be a PIN photodiode, an MIS sensor, or any other element.

This application claims priority from Japanese Patent Application No. 2004-107201 filed Mar. 31, 2004, which is hereby incorporated by reference herein.

What is claimed is:

1. An image radiographing apparatus comprising:
an area sensor;
radiographing mode setting means for selecting one radiographing mode from among a plurality of radiographing modes that are preset;
correction means for performing an arithmetic operation processing using a radiographed output and an offset output from said area sensor; and
control means for controlling said area sensor and the arithmetic operation processing by said correction means in accordance with a signal from said radiographing mode setting means,
wherein at least one of the plurality of radiographing modes is an energy subtraction radiographing mode in which the radiographed output of at least two frames acquired by different x-ray energies and the offset output of at least one frame are acquired.

2. The image radiographing apparatus according to claim 1, wherein said control means enables said correction means to perform the arithmetic operation processing using the offset output in accordance with a signal from said radiographing mode setting means.

3. The image radiographing apparatus according to claim 2, wherein the offset output in accordance with the signal from said radiographing mode setting means is an offset output obtained by the reading operation immediately after acquiring the radiographed output.

4. The image radiographing apparatus according to claim 2, wherein the offset output in accordance with the signal from said radiographing mode setting means is an offset output obtained by the reading operation immediately before acquiring the radiographed output.

5. The image radiographing apparatus according to claim 2, wherein the offset output in accordance with the signal from said radiographing mode setting means is a preset offset output before acquiring the radiographed output.

6. The image radiographing apparatus according to claim 5, wherein the preset offset output is an average of the offset outputs of at least two frames.

7. The image radiographing apparatus according to claim 1, wherein at least one of the plurality of radiographing modes is a moving image radiographing mode in which the radiographed output and the offset output are repeatedly acquired.

8. The image radiographing apparatus according to claim 7, wherein said control means enables said correction means to perform the arithmetic operation processing using the radiographed output and the offset output obtained by the reading operation immediately after acquiring the radiographed output in the moving image radiographing mode.

9. The image radiographing apparatus according to claim 7, wherein said control means enables said correction means to perform the arithmetic operation processing using the radiographed output and the offset output obtained by the reading operation immediately before acquiring the radiographed output in said moving image radiographing mode.

10. The image radiographing apparatus according to claim 1, wherein at least one of the plurality of radiographing modes is a high speed moving image radiographing mode in which the radiographed output is repeatedly acquired, wherein the high speed moving image radiographing mode is higher speed than a moving image radiographing mode in which the radiographed output and the offset output are repeatedly acquired.

11. The image radiographing apparatus according to claim 10, wherein said control means enables said correction means to perform the arithmetic operation processing using the radiographed output and a preset offset output in the high speed moving image radiographing mode.

12. The image radiographing apparatus according to claim 1, wherein at least one of the plurality of radiographing modes is a still image radiographing mode in which the radiographed output of one frame and the offset output of at least one frame are acquired.

13. The image radiographing apparatus according to claim 12, wherein said control means enables said correction means to perform the arithmetic operation processing using the radiographed output and the offset output obtained by the reading operation immediately after acquiring the radiographed output in the still image radiographing mode.

14. The image radiographing apparatus according to claim 1, wherein said control means enables said correction means to perform the arithmetic operation processing using the radiographed output and the offset output obtained by the reading operation immediately after acquiring the radiographed output in the energy subtraction radiographing mode.

15. The image radiographing apparatus according to claim 1, wherein said correction means comprises at least one or more radiographed output memories for storing the radiographed output and one or more offset memories for storing the offset output.

16. The image radiographing apparatus according to claim 1, further comprising a radiographing condition memory for storing the radiographing conditions when acquiring the radiographed output, in which said control means controls the operation of said area sensor in accordance with the storage contents of radiographing condition memory to acquire said the offset output.

17. The image radiographing apparatus according to claim 16, further comprising automatic exposure control means, in which said control means enables the information from said automatic exposure control means to be stored as one kind of the radiographing conditions in said radiographing condition memory.

18. An image radiographing system comprising:
   an X-ray generator;
   an area sensor;
   radiographing mode setting means for setting one radiographing mode from among a plurality of radiographing modes that are preset;
   correction means for performing an arithmetic operation processing using a radiographed output and an offset output from said area sensor; and
   control means for controlling said X-ray generator, said area sensor and the arithmetic operation processing by said correction means in accordance with a signal from said radiographing mode setting means,
   wherein at least one of the plurality of radiographing modes is an energy subtraction radiographing mode in which the radiographed output of at least two frames acquired by different x-ray energies and the offset output of at least one frame are acquired.

* * * * *

UNITED STATES PATENT AND TRADEMARK OFFICE
CERTIFICATE OF CORRECTION

| | | |
|---|---|---|
| PATENT NO. | : 7,227,926 B2 | Page 1 of 2 |
| APPLICATION NO. | : 11/088775 | |
| DATED | : June 5, 2007 | |
| INVENTOR(S) | : Toshio Kameshima et al. | |

It is certified that error appears in the above-identified patent and that said Letters Patent is hereby corrected as shown below:

ON TITLE PAGE AT (57) ABSTRACT

Line 10, "106" should be deleted.

COLUMN 3

Line 20, "x-ray" should read --X-ray--;
　　Line 36, "x-ray" should read --X-ray--; and
　　Line 52, "x-ray" should read --X-ray--.

COLUMN 4

Line 2, "x-ray" should read --X-ray--.

COLUMN 9

Line 10, "-to" should read --to--.

COLUMN 10

Line 13, "(step S47) .," should read --(step S47).--.

COLUMN 11

Line 26, ""radiographed output X-offset output F1"," should read
　　　　--"radiographed output X1-offset output F1",--; and
　　Line 40, "S75) Then," should read --S75). Then,--

COLUMN 12

Line 43, "x-ray" should read --X-ray--.

UNITED STATES PATENT AND TRADEMARK OFFICE
CERTIFICATE OF CORRECTION

PATENT NO. : 7,227,926 B2
APPLICATION NO. : 11/088775
DATED : June 5, 2007
INVENTOR(S) : Toshio Kameshima et al.

It is certified that error appears in the above-identified patent and that said Letters Patent is hereby corrected as shown below:

<u>COLUMN 14</u>

Line 16, "radiographing" should read --said radiographing--;
Line 17, "said" should be deleted; and
Line 40, "x-ray" should read --X-ray--.

Signed and Sealed this

Twenty-fifth Day of March, 2008

JON W. DUDAS
*Director of the United States Patent and Trademark Office*